(12) United States Patent
Weber et al.

(10) Patent No.: US 11,407,730 B2
(45) Date of Patent: *Aug. 9, 2022

(54) PREPARATION OF RACEMIC NICOTINE BY REACTION OF ETHYL NICOTINATE WITH N-VINYLPYRROLIDONE IN THE PRESENCE OF AN ALCOHOLATE BASE AND SUBSEQUENT PROCESS STEPS

(71) Applicants: SIEGFRIED AG, Zofingen (CH); CONTRAF-NICOTEX-TOBACCO GMBH, Heilbronn (DE)

(72) Inventors: Beat Theodor Weber, Zofingen (CH); Christian Lothschütz, Rheinfelden (CH); Ben Pan, Nantong (CN)

(73) Assignees: Siegfried AG, Zofingen (CH); Contraf-Nicotex-Tobacco GmbH, Heilbronn (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/957,006

(22) PCT Filed: Dec. 18, 2018

(86) PCT No.: PCT/EP2018/085437
§ 371 (c)(1),
(2) Date: Jun. 22, 2020

(87) PCT Pub. No.: WO2019/121644
PCT Pub. Date: Jun. 27, 2019

(65) Prior Publication Data
US 2020/0331884 A1   Oct. 22, 2020

(30) Foreign Application Priority Data
Dec. 22, 2017 (EP) ................. 17210187

(51) Int. Cl.
*C07D 401/04* (2006.01)
(52) U.S. Cl.
CPC ............... *C07D 401/04* (2013.01)
(58) Field of Classification Search
CPC .................................... C07D 401/04
USPC ..................................... 546/279.4
See application file for complete search history.

(56) References Cited

U.S. PATENT DOCUMENTS

| | | | |
|---|---|---|---|
| 5,734,059 A | 3/1998 | Watanabe et al. | |
| 8,378,111 B2 | 2/2013 | Divi et al. | |
| 8,884,021 B2 | 11/2014 | Tian et al. | |
| 9,556,142 B2 * | 1/2017 | Arnold ............... | C07D 401/04 |
| 2006/0135617 A1 | 6/2006 | Kamiyama et al. | |
| 2012/0209006 A1 | 8/2012 | Divi et al. | |
| 2014/0031554 A1 | 1/2014 | Tian et al. | |
| 2016/0326134 A1 | 11/2016 | Willis et al. | |
| 2020/0331883 A1 | 10/2020 | Weber et al. | |

FOREIGN PATENT DOCUMENTS

| | | |
|---|---|---|
| CN | 102617547 | 8/2012 |
| EP | 2 484 673 | 8/2012 |
| EP | 2 487 172 | 5/2014 |
| JP | 08-92242 | 4/1996 |
| JP | 2003-342259 | 12/2003 |
| JP | 2006-335639 | 12/2006 |
| JP | 2006335639 | 12/2006 |
| JP | 2017-531672 | 10/2017 |
| WO | WO 2012/100722 | 8/2012 |
| WO | WO 2016/064935 A1 | 4/2016 |
| WO | WO 2016/065209 | 4/2016 |
| WO | WO 2017/117575 | 7/2017 |
| WO | WO 2017/119003 | 7/2017 |
| WO | WO2019/121649 | 6/2019 |

OTHER PUBLICATIONS

Aceto M. D., et al., J. Med. Chem., 1979, vol. 22, No. pp. 174-177.
Berichte derdeutschen chemischen Gesellschaft, vol. 37, 1904, pp. 1225-1235.
Bowman E.R. et al., Synthetic Comm., 1982, vol. 12, No. 11, pp. 871-879.
Chavdarian C. G. et al., J. Org. Chem.,1982, vol. 41, 1069-1073).
Desai D. et al., J. Labeled Compd. Radiopharm., 2008, vol. 51, 226-230.
Glassco W. et al. (1993) J. Med. Chem. 36, 22, 3381-3385.
Hatton et al. (2009) Synthesis of four racemic nicotine isotopomers doubly labelled with stable isotope. J. Label Compd. Radiopharm. 52:117-122.
International Preliminary Report on Patentability corresponding to International Patent Application No. PCT/EP2018/085437 dated Jun. 23, 2020.
International Preliminary Report on Patentability corresponding to International Patent Application No. PCT/EP2018/085444 dated Jun. 23, 2020.
International Search Report corresponding to International Patent Application No. PCT/EP2018/085437 dated Feb. 20, 2019.
International Search Report corresponding to International Patent Application No. PCT/EP2018/085444 dated Feb. 20, 2019.
Katsuyama A. et al., Bull. Spec. CORESTA Symposium, Winston-Salem, 1982, p. 15, So5, ISSN 0525-6240.
Nenajdenko et al., "Synthesis and the Keto-Enol Equilibrium of 2-Acyl Lactams", Russian Chemical Bull., vol. 52, No. 11, pp. 2473-2482 (Nov. 2003).
Office Action corresponding to Indian Patent Application No. 202047026902 dated Jan. 18, 2021.
Office Action corresponding to U.S. Appl. No. 16/956,964 dated Oct. 26, 2020.
Office Action corresponding to U.S. Appl. No. 16/956,964 dated Mar. 25, 2021.
Pictet, A. (1904) Berichte derdeutschen chemischen Gesellschaft, vol. 37, pp. 1225-1235.

(Continued)

*Primary Examiner* — Nizal S Chandrakumar
(74) *Attorney, Agent, or Firm* — Jenkins, Wilson, Taylor & Hunt, P.A.

(57) ABSTRACT

The present invention relates to a method of preparing racemic nicotine comprising: (i) reacting ethyl nicotinate and N-vinylpyrrolidone in the presence of an alcoholate base to 3-nicotinoyl-1-vinylpyrrolidin-2-one; (ii) reacting the 3-nicotinoyl-1-vinylpyrrolidin-2-one with an acid to myosmine; (iii) reducing the myosmine to nornicotine using a reducing agent; and (iv) methylating the nornicotine to obtain the racemic nicotine.

17 Claims, No Drawings

(56) References Cited

OTHER PUBLICATIONS

Wang J. et al., "Design, synthesis and biological evaluation of aminobenzyloxyarylamide derivatives as selective Kopiod receptor antagonists", E. J Med. Chern., 2017, vol. 130,15-25.
Written Opinion of the International Searching Authority corresponding to International Patent Application No. PCT/EP2018/085437 dated Jun. 27, 2019.
Written Opinion of the International Searching Authority corresponding to International Patent Application No. PCT/EP2018/085444 dated Jun. 27, 2019.
Examination Report corresponding to Australian Patent Application No. 2018391652 dated Jun. 21, 2021.
Notice of Allowance corresponding to U.S. Appl. No. 16/956,964 dated Jul. 14, 2021.
Office Action corresponding to Indian Patent Application No. 202047025938 dated Mar. 22, 2021.
Examination Report corresponding to Australian Patent Application No. 2018391657 dated Jun. 21, 2021.
Search Report corresponding to European Patent Application No. 17210187.5 dated May 8, 2018.
Examination Report corresponding to European Patent Application No. 18816112.9 dated May 11, 2021.
Office Action corresponding to Belarus Patent Application No. 20200195 dated Jan. 20, 2022.
Office Action corresponding to Belarus Patent Application No. 20200196 dated Jan. 20, 2022.
Office Action corresponding to Chilean Patent Application No. 202001656 dated Oct. 26, 2021.
Office Action corresponding to Chilean Patent Application No. 202001657 dated Oct. 18, 2021.
Office Action corresponding to Indonesian Patent Application No. P00202004544 dated Dec. 6,2 021.
Office Action corresponding to Indonesian Patent Application No. P00202004545 dated Dec. 6, 2021.
Office Action corresponding to Japanese Patent Application No. 2020-554569 dated Jan. 11, 2022.
Office Action corresponding to Japanese Patent Application No. 2020-554570 dated Oct. 28, 2021.
Search Report corresponding to Chilean Patent Application No. 202001656 dated Oct. 26, 2021.
Search Report corresponding to Chilean Patent Application No. 202001657 dated Oct. 18, 2021.
Search Report corresponding to Russian Patent Application No. 2020120637/04 (035217) dated Feb. 15, 2021.
Smirnova et al. (2012) "Optical Isomerism and Biological Activity of Medicines," Bulletin of Moscow University, Series 2, Chemistry, vol. 53, No. 3, 12, pp. 147-156.
Written Opinion corresponding to Singapore Patent Application No. 11202005641X dated Mar. 29, 2021.
Interview Summary corresponding to U.S. Appl. No. 16/956,964 dated Mar. 21, 2022.
Office Action corresponding to Chilean Patent Application No. 202001657 dated Apr. 18, 2022.
Search Report corresponding to Chilean Patent Application No. 202001657 dated Apr. 18, 2022.

* cited by examiner

PREPARATION OF RACEMIC NICOTINE BY REACTION OF ETHYL NICOTINATE WITH N-VINYLPYRROLIDONE IN THE PRESENCE OF AN ALCOHOLATE BASE AND SUBSEQUENT PROCESS STEPS

CROSS REFERENCE TO RELATED APPLICATIONS

This application is a national stage filing of PCT International Application No. PCT/EP2018/085437, filed Dec. 18, 2018, which is based on and claims priority to European Patent Application Serial No. 17210187.5, filed Dec. 22, 2017.

FIELD OF THE INVENTION

The present invention relates to a method of preparing a compound of Formula I-a, including a method for separating the mixture of enantiomers represented by Formula I-a into the enantiomerically pure substances represented by Formula I-b and Formula I-c.

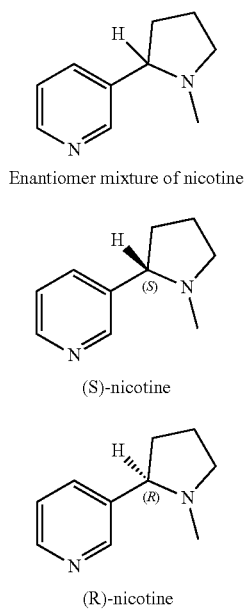

Formula I-a

Enantiomer mixture of nicotine

Formula I-b (S)-nicotine

Formula I-c (R)-nicotine

The present invention relates particularly to an environmental friendly and efficient method of preparing nicotine of Formulae I-a. Nicotine is obtained in pure form avoiding the use of harmful chemicals during synthesis.

The invention further relates to a method of preparing racemic mixtures of (R/S)-nicotine, enantiomerically pure (R)-nicotine, and enantiomerically pure (S)-nicotine, where the enantiomers are generally are difficult to separate.

BACKGROUND OF THE INVENTION

Nicotine is a naturally occurring alkaloid used in various applications. Especially (S)-nicotine is used as active pharmaceutical ingredient to treat nicotine abuse and nicotine dependency. Success has further been reported when treating Tourette's syndrome, Alzheimer's disease, schizophrenia and other diseases related to disorders of the nervous system. Common ways of administration are gums, creams, transdermal patches, tablets, nasal sprays, and electric cigarettes.

Considerable quantities of nicotine are also used in agriculture as plant protectant or pesticide against aphids.

Natural nicotine is extracted from tobacco plants, a process that requires efficient purification steps to remove undesired, harmful impurities. The increasing demand of nicotine creates a need to offer ecological and economical ways to prepare synthetic nicotine in very pure form.

STATE OF THE ART

Nicotine ((S)-3-(1-methylpyrrolidin-2-yl)pyridine) and its enantiomers have been prepared for many years by various, not satisfying methods. Known syntheses are usually expensive and use agents that are problematic or even toxic for the environment.

Pictet A. reported in 1904 already a synthesis for nicotine, including the use of tartaric acid to separate the enantiomers (Berichte der deutschen chemischen Gesellschaft, vol. 37, 1904, pages 1225-1235). Tartaric acid has then been used afterwards for decades (see for example: Aceto M. D., et al. (J. Med. Chem., 1979, vol. 22, 174-177)).

More recently Chavdarian C. G. et al. disclosed more modern ideas on the synthesis of optically active nicotinoids (J. Org. Chem., 1982, vol. 41, 1069-1073).

Katsuyama A. et al. reported a way of synthesizing nicotine using potassium tert-butanolate for the racemization of nicotine to prepare the starting material for further separation of the enantiomers (Bull. Spec. CORESTA Symposium, Winston-Salem, 1982, p. 15, S05, ISSN 0525-6240).

Further, EP 4 487 172 discloses a synthesis route over 5 different steps, offering a net yield of 37.7%.

WO 2017/117575 discloses a synthesis of nicotine using potassium hydride (KH) or sodium hydride (NaH) as strong base in tetrahydrofuran (THF) as solvent to obtain nicioti-noyl-1-vinylpyrrolidin-2-one. Yield of (R/S)-nicotine is about 31%. Similar procedures as well as procedures for enantiomeric separation of the nicotine have been disclosed by Wang J. et al. (Wang J. et al., E. J Med. Chem., 2017, vol. 130, 15-25), by Desai D. et al. (Desai D. et al., J. Labeled Compd. Radiopharm, 2008, vol. 51, 226-23), Aceto M. D. et al., (Aceto M. D. et al., J. Med. Chem., 1979, vol. 2, 174-177) or by Bowman E. R. et al. (Bowman E. R. et al., Synthetic Comm., 1982, vol. 12, 11, 871-879), In US 2016/0326134 a synthesis comprising the condensation of 1-methylpyrrolidin-2-one and methyl nicotinate in the presence of a strong base (as K tert-butoxide) at reflux to the intermediate potassium 1-methyl-3-nicotinoyl-4,5-dihydro-1H-pyrrol-2-late is described, which then can be converted into the racemic mixture of R/S nicotine. Di-para-toluoyl-L-tartaric acid serves as resolution agent.

EP 2 484 673 (U.S. Pat. No. 8,378,111) relies on well-known routes of synthesis and discloses D-DBTA (D-dibenzoyl ester of tartaric acid) as agent to separate the enantiomers.

WO 2016/65209 (EP 3 209 653, U.S. Pat. No. 9,556,142) discloses a preparative way comprising 3 steps to the intermediate myosmine, including the condensation of N-vinylegous-pyrrolidinone and nicotinate ester in the presence of a metal hydride.

During the last years development was mainly focused on purification and optimization of the resolution step of the optically active enantiomers. But there is a need for improvement towards a more efficient, more ecologic synthesis of nicotine and the use of environmental friendly agents and solvents.

SUMMARY OF THE INVENTION

The current invention offers a novel method for preparing nicotine, including a specific process to separate the enantiomers manufactured. Inventors found a method having less synthetic steps based on easily accessible starting materials, and less toxic agents compared to those disclosed in literature. The whole synthesis can be executed as one-pot synthesis, particularly without changing the solvent in different steps. At the same time increased yield and a high purity of the final report has been found. Overall the novel method is economically and ecologically superior compared to methods known in the art.

In a first aspect, the present invention relates to a method of preparing a compound of Formula I-a, comprising

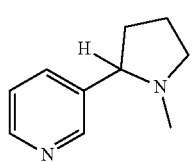

(I-a)

(i) reacting ethyl nicotinate and N-vinylpyrrolidone in the presence of an alcoholate base to 3-nicotinoyl-1-vinylpyrrolidin-2-one;
(ii) reacting the 3-nicotinoyl-1-vinylpyrrolidin-2-one with an acid to myosmine;
(iii) reducing the myosmine to nornicotine using a reducing agent; and
(iv) methylating the nornicotine to obtain the compound of Formula I-a.

Further embodiments are disclosed in the dependent claims and can be taken from the following description and examples, without being limited thereto.

DETAILED DESCRIPTION OF THE PRESENT INVENTION

If not defined otherwise technical and scientific terms have the same meaning as is generally understood by a skilled person in the field of the invention.

All ranges disclosed herein are to be considered to be supplemented by the term "about", unless clearly defined to the contrary or otherwise clear from the context.

All numbers or percentages relating to amounts of a substance within this application are given in wt. %, unless clearly defined to the contrary or otherwise clear from the context.

The current invention offers a novel method for manufacturing nicotine in a convenient way.

In addition, the invention relates in a further aspect to the use of the compound as represented by Formula I-a, Formula I-b or Formula I-c obtained by the method according to the invention in a pharmaceutical formulation.

In a first aspect, the present invention relates to a method of preparing a compound of Formula I-a, comprising

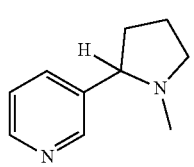

(I-a)

(i) reacting ethyl nicotinate and N-vinylpyrrolidone (NVP) in the presence of an alcoholate base to 3-nicotinoyl-1-vinylpyrrolidin-2-one;
(ii) reacting the 3-nicotinoyl-1-vinylpyrrolidin-2-one with an acid to myosmine;
(iii) reducing the myosmine to nornicotine using a reducing agent; and
(iv) methylating the nornicotine to obtain the compound of Formula Ia.

Step (i) is therein as follows:

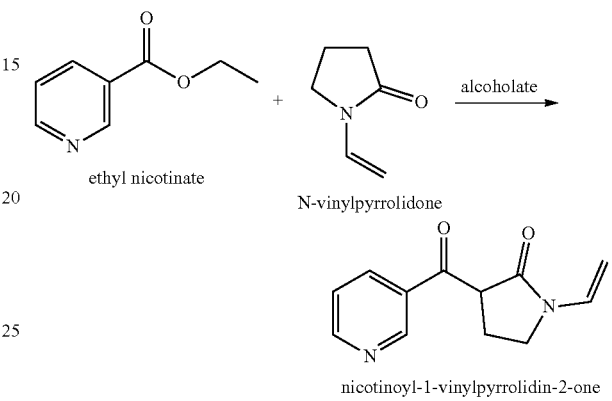

The alcoholate base in step (i) is not particularly restricted. It can be an alcoholate (also known as alkoxide) having 1 to 20 carbon atoms and can be derived from a primary, secondary or tertiary alkyl, alkenyl and/or alkinyl alcohol and/or an aromatic alcohol. Noting that staring materials as N-vinylpyrrolidone are medium strong bases (typical pKa values between 20 and 26, in some cases up to 35), inventors surprisingly found that the relatively gentle basic alcoholates (typical pKa values between 15 and 17) allow the same selective chemical reaction than more aggressive bases as NaH or KH for example (pKa values at about 35). According to certain embodiments, the alcoholate base is derived from an alkyl alcohol having 1 to 20 carbon atoms, preferably 1 to 10 carbon atoms, further preferably 1 to 6 carbon atoms, particularly 1 to 4 carbon atoms, wherein the alkyl can be linear or branched. For example it can be a methanolate, ethanolate, n-propanolate, iso-propanolate, n-butanolate, iso-butanolate, sec-butanolate, tert-butanolate, etc., preferably methanolate and ethanolate, further preferably ethanolate (also known as ethoxide). The alcoholate can have a suitable cation which is not particularly restricted and can be e.g. chosen from monovalent and divalent cations, e.g. of alkali and alkaline earth metal cations, preferably alkali metal cations, further preferably Li$^+$, Na$^+$, K$^+$ and mixtures thereof. Suitable preferred alcoholates are preferably alkali metal alcoholates, preferably alkali metal ethanolates.

Preferably the alkali metal alcoholate is chosen from sodium ethanolate, potassium ethanolate, and mixtures thereof. In one aspect, it has been found that sodium ethanolate is a suitable base which is particularly preferred.

Step (i) can be carried out in a suitable solvent that is not particularly restricted. According to certain embodiments, step (i) is carried out in the presence of an aromatic solvent. A preferred aromatic solvent is benzene, toluene, or a mixture thereof. In a preferred aspect of the invention toluene is chosen as solvent. Also mixtures of aromatic solvents with non-aromatic solvents are usable. For example, mixtures of an aromatic solvent with up to and including 15 wt. % of at least an alcohol, e.g. a monohydric alcohol with 1 to 10 carbon atoms, e.g. ethanol, n-propanol, and/or i-propanol, etc., can be used.

According to certain embodiments, the aromatic solvent used in step (i) is present in all of steps (i), (ii), (iii) and (iv) of the present method at least to some extent.

According to certain embodiments, step (i) is carried out under anhydrous conditions, i.e. in the absence of water.

According to certain embodiments, step (i) is carried out at a temperature between 50 and 150° C., preferably between 80 and 120° C., further preferably between 90 and 110° C., e.g. at about 100° C.

According to certain embodiments, the alcoholate base is added in step (i) in excess over the ethyl nicotinate, preferably in an amount of between 1.4 and 2 equivalents, further preferably in an amount between 1.5 and 17 equivalents, particularly preferably 1.6 equivalents, based on 1 equivalent of the ethyl nicotinate. According to certain embodiments, alternatively or in addition NVP is added in step (i) in excess over the ethyl nicotinate, preferably in an amount between 1.05 and 1.4 equivalents, further preferably in an amount between 1.1 and 1.3 equivalents, particularly preferably 1.2 equivalents, based on 1 equivalent of the ethyl nicotinate.

Step (ii) is as follows:

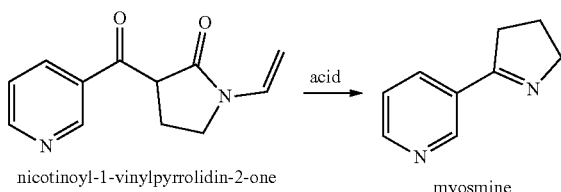

In step (ii) the 1-pyrroline ring is formed, the amide deprotected, and the nicotinoyl-1-vinylpyrrolidin-2-one is decarboxylated.

According to certain embodiments step (ii) is performed at increased temperature in the presence of an acid, preferably a strong acid. In some aspects the temperature is between 90 and 115° C., preferably between 100° C. and 105° C. It is understood that at elevated temperature a part of the solvent, e.g. organic solvent of step (i) and e.g. a part of water added with the acid can be removed by distillation and can be recovered and reused. Also, low boiling components like acetaldehyde, ethanol and gaseous CO$_2$ can be removed.

In this step the acid is not particularly restricted. According to certain embodiments, the acid is an inorganic acid, preferably a mineralic acid, further preferably HCl and/or H$_2$SO$_4$, particularly preferably HCl. The acid can be diluted in water, e.g. be present as HCl$_{aq}$. According to certain embodiments, the acid is added dropwise to a cooled solution obtained in step (i), e.g. cooled down to a temperature between 20 and 40° C., e.g. to 30° C. According to certain embodiments, the mixture obtained in step (i) or nicotinoyl-1-vinylpyrrolidin-2-one—optionally in a suitable solvent, as above—is added dropwise to the acid, preferably inorganic acid, further preferably mineralic acid, even further preferably HCl and/or H$_2$SO$_4$, particularly preferably HCl, e.g. HCl$_{aq}$, which can lead to an increased yield.

According to certain embodiments, step (ii) is carried out using an inorganic acid, particularly preferably HCl$_{aq}$ at a temperature between 90 and 115° C., preferably between 100 and 105° C.

After the reaction in step (ii) is finished, at least a part of the solvents can be removed by distillation according to certain embodiments.

Step (iii) is as follows:

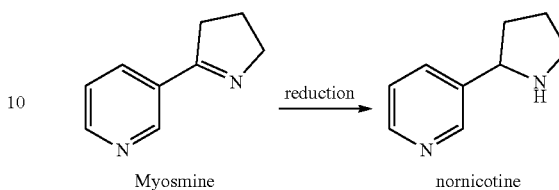

In step (iii) the 1-pyrroline ring of myosmine is reduced by a suitable reduction agent that is not particularly restricted. According to certain embodiments reduction of the 1-pyrroline ring is made using a standard method. According to certain embodiments, step (iii) is carried out using NaBH$_4$ as reducing agent. As there are different methods inventors found that according to some aspects of the invention NaBH4, particularly in iso-propanol, offered an opportunity to follow the one-pot reaction concept. The use of this reducing agent is thus particularly preferred if the present method is carried out in a one-pot process without any purification steps of the intermediates. According to certain embodiments, the reaction is carried out at temperatures between 18° C. and 30° C., preferably at temperatures between 20° and 25° C.

Step (iv) is as follows:

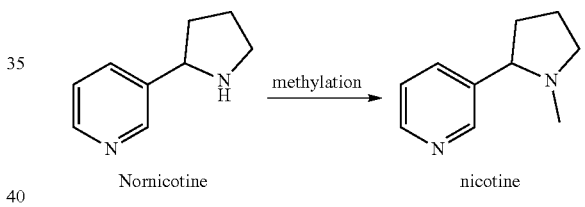

In step (iv) the pyrrolidine ring is methylated at the N-atom by a suitable methylating agent, which also is not particularly restricted. In this step the nicotine can be formed as a mixture of the (R)- and (S)-enantiomer thereof According to certain embodiments, step (iv) is carried out using formic acid and paraformaldehyde, or formic acid and formaldehyde, preferably at a temperature between and including 40 to 95° C., further preferably between and including 60 to 85° C., even further preferably at a temperature from 60 to 70° C., even further preferably at 65±2° C.

One aspect of the invention is that no additional solvent needs to be added to the reaction mixture in this step, not increasing the amount of the solvent already being present in the mixture, and/or not adding a different solvent.

According to certain embodiments the reaction is run at preferably increased temperatures, temperatures above room temperature. It has been found that temperatures are preferably between 40 and 95° C., further preferably between 60° C. and 85° C., even further preferably between 60° C. and 70° C., and most preferably the temperature is at 65° C.±2° C. to get desirable results.

According to certain embodiments, the present method can be carried out in a one-pot process. This saves of course further separating steps, solvents, energy and time. Particularly a one-pot process can be achieved with the preferred steps given above. It has been surprisingly found that the whole synthesis can be made as a one-pot process without any purification steps of the intermediates in such embodiments. One specific further advantage of the invention is the one-pot synthesis allowing a straight forward reaction sequence and using minimal amounts and types of solvents. According to certain embodiments, no solvent change is necessary in such a one-pot process.

According to certain embodiments, the compound of Formula I-a or the compound of Formula I-c, i.e. the mixture of nicotine enantiomers or the nicotine in the enantiopure (R)-form, is further reacted with an organic base at a temperature between 140 and 160° C. This way a "racemization" of the obtained mixture can take place, i.e. it can be shifted in the direction of a racemic mixture. According to certain embodiments, (R)-nicotine can be shifted to (S)-nicotine in this step. This reaction can take place with the formed mixture, the compound of Formula I-a, but also with e.g. essentially pure (R)-nicotine, which can be e.g. obtained after separating (S)-nicotine from the mixture of enantiomers of nicotine, as described below.

The organic base is not particularly restricted. It can be an alcoholate having 1 to 20 carbon atoms and can be derived from a primary, secondary or tertiary alkyl, alkenyl and/or alkinyl alcohol and/or an aromatic alcohol. According to certain embodiments, it is derived from an alkyl alcohol having 1 to 20 carbon atoms, preferably 1 to 10 carbon atoms, further preferably 1 to 6 carbon atoms, particularly 1 to 4 carbon atoms, wherein the alkyl can be linear or branched. For example it can be a methanolate, ethanolate, n-propanolate, iso-propanolate, n-butanolate, iso-butanolate, sec-butanolate, tert-butanolate, etc., preferably butanolate, further preferably tert-butanolate. The alcoholate can have a suitable cation which is not particularly restricted and can be e.g. chosen from monovalent and divalent cations, e.g. of alkali and alkaline earth metal cations, preferably alkali metal cations, further preferably $Li^+$, $Na^+$, $K^+$ and mixtures thereof. Suitable preferred alcoholates are preferably alkali metal alcoholates, preferably alkali metal tert-butanolates. Preferably the alkali metal alcoholate is chosen from sodium tert-butanolate, potassium tert-butanolate, and mixtures thereof. In one aspect, it has been found that potassium tert-butanolate is a suitable base in this step which is particularly preferred.

The organic base can be supplied either neat, i.e. without additional solvent—particularly if already solvent from a one-pot process is still contained, or in a suitable solvent which is not particularly restricted. Aromatic solvents like benzene and toluene are preferred, and toluene is particularly preferred as solvent. Also aromatic solvents containing non-aromatic solvents are suitable.

According to certain aspects of the invention is has been found that the "racemization" can take places place at moderate temperatures, i.e. without heating to reflux of nicotine. Inventors found that using tert-butoxide in toluene racemising (R)-nicotine into a 45:55 to 55:45 mixture of (S)- and (R)-nicotine can be carried out at a temperature between 130 and 180° C., preferably 140 to 170° C., further preferably 140 to 160° C.

According to certain embodiments the mixture of nicotine enantiomers, e.g. racemic nicotine, can be separated by an inventive method using economically and ecologically advantageous agents.

According to certain embodiments, the present method thus further comprises separating enantiomers of the compound of formula I-a by addition of a chiral O,O'-disubstituted tartaric acid, preferably dibenzoyl tartaric acid or ditoluoyl tartaric acid or mixtures thereof.

The nicotine of Formula I-a is not particularly restricted and can be obtained by the above method. It is a mixture of the (R)- and (S)-enantiomer of nicotine that is not particularly limited and which can comprise the two enantiomers at any ratio, as long as both enantiomers are contained. It can be a racemic mixture, i.e. a mixture with a molar ratio of 50:50, but it can also be a mixture with a ratio of the (S)-enantiomer to the (R)-enantiomer in the range of e.g. 1:99 to 99:1, e.g. 10:90 to 90:10, e.g. 20:80 to 80:20, e.g. 30:70 to 70:30, e.g. 40:60 to 60:40, e.g. 45:55 to 55:45, or any other ratio in between these ratios. The present method allows the separation of the (S)-enantiomer out of this mixture.

The chiral O,O'-disubstituted tartaric acid is not particularly limited as long as it is chiral, i.e. optically active, and it does not have to be enantiopure. The two substituents on the oxygen of the hydroxy groups are not particularly limited and can be the same or different. According to certain embodiments they are chosen from alkyl groups with 1 to 20 C-atoms, alkenyl and/or alkinyl groups with 2 to 20 C-atoms, aryl groups with 6 to 20 C-atoms; and/or alkyl aryl and/or aryl alkyl groups with 7 to 20 C-atoms that all can be substituted or unsubstituted by functional groups like halogen groups, nitro groups, amine groups, ester groups, amide groups, etc., and which all are preferably unsubstituted. Preferred substituents in the chiral O,O'-disubstituted tartaric acid are aryl groups with 6 to 20 C-atoms; and/or alkyl aryl and/or aryl alkyl groups with 7 to 20 C-atoms that are not substituted.

According to certain embodiments, the chiral O,O'-disubstituted tartaric acid is chosen from O,O'-dibenzoyl tartaric acid and O,O'-ditoluoyl tartaric acid, e.g. O,O'-di-o-toluoyl tartaric acid, O,O'-di-m-toluoyl tartaric acid and/or O,O'-di-p-toluoyl tartaric acid, and or mixtures thereof, preferably O,O'-dibenzoyl tartaric acid. According to certain embodiments, it is added in ethanol as solvent.

In the present method the chiral O,O'-disubstituted tartaric acid comprises preferably the L-enantiomer. The O,O'-disubstituted tartaric acid can in this case either consist of the L-enantiomer or comprise the L-enantiomer and the D-enantiomer as a mixture. In the latter case, it is preferable that the L-enantiomer is contained in excess of the D-enantiomer, e.g. at a molar ratio of L-enantiomer to D-enantiomer of at least 80:20, preferably at least 9:0, wherein this ratio can also be described as enantiomeric excess (ee) of at least 60%, preferably at least 80%.

According to certain embodiments, the chiral O,O'-disubstituted tartaric acid is O,O'-dibenzoyl-L-tartaric acid, i.e. has an ee of 100%. According to certain embodiments, it is added in ethanol as solvent.

While it has been found that the separation of the (R)- and (S)-nicotine can be achieved with a separating agent that is a pure enantiomer, i.e. the L-enantiomer of the chiral O,O'-disubstituted tartaric acid if the (S)-nicotine is to be obtained, it has also surprisingly been found that the same is also accomplished if not a pure separating agent, also termed resolution agent, is used, but also when a mixture of enantiomers of the chiral O,O'-disubstituted tartaric acid is used, which surprisingly achieved the separation effect. Even though pure separating agents/resolution agents are available, there is an advantage in using the economically and ecologically easier accessible agents as mixtures with an excess of one enantiomer, e.g. the L-enantiomer if the (S)-nicotine (compound of formula I-b) is to be obtained.

According to certain embodiments, the O,O'-disubstituted tartaric acid is a mixture of the L-enantiomer and the D-enantiomer, wherein the L-enantiomer is contained in excess over the D-enantiomer, preferably wherein the molar ratio of the L-enantiomer to the D-enantiomer is 80:20 or more, preferably 90:10 or more. According to certain embodiments, it is added in ethanol as solvent.

According to certain embodiments, the O,O'-disubstituted tartaric acid is a mixture of O,O'-dibenzoyl-L-tartaric acid (L-DBTA) and O,O'-dibenzoyl-D-tartaric acid (D-DBTA) with a molar ratio of L-DBTA to D-DBTA of 80:20 or more, preferably 90:10 or more. According to certain embodiments, it is added in ethanol as solvent.

In the present method, the solvent used for adding the O,O'-disubstituted tartaric acid is not particularly restricted and can be any suitable solvent in which the O,O'-disubstituted tartaric acid can be dissolved. According to certain embodiments, the solvent is ethanol. For the separation, the mixture obtained by adding the O,O'-disubstituted tartaric acid to the compound of Formula I-a can be e.g. refluxed over a certain time period to react the mixture.

After this step the compound of Formula I-b can be obtained from this reacted mixture. The obtaining of the compound of Formula I-b is not particularly restricted and can be carried out by suitable methods, e.g. hydrolyzing the obtained salt of the (S)-nicotine with the separating agent with water in alkaline medium, extracting with an organic solvent like toluene, and distilling of the solvent. For obtaining the salt of the (S)-nicotine with the separating agent, it can be precipitated beforehand, filtered, and optionally washed, e.g. with ethanol. The steps of precipitating, filtering and washing therein can be carried out repeatedly, e.g. two, three, four or more times.

An exemplary reaction scheme for the present method is presented hereunder:

According to this scheme, a mixture of enantiomers of nicotine can be synthesized in a one-pot process (steps 1a-d) starting with a condensation of ethyl nicotinate and 1-vinyl-2-pyrrolidone in the presence of a base, e.g. EtONa (step 1a). In the presence of a strong acid like HCl, e.g. $HCl_{aq}$, the amide nitrogen is deprotected and decarboxylation takes place (step 1b). Reduction of the pyrroline ring to a pyrrolidine ring is performed, e.g. with $NaBH_4$ in iso-propanol (step 1c), followed by methylation to nicotine, e.g. with formic acid and paraformaldehyde (step 1d), or formic acid and formalydehyde. The racemic mixture of nicotine enantiomers, e.g. a racemic mixture, can be resolved with a resolving agent like L-DBTA to obtain the target product (S)-nicotine (step 2). The obtained (R)-nicotine can be recycled by racemization using a base (step 3) and undergoing a further resolving step.

The above embodiments can be combined arbitrarily, if appropriate. Further embodiments and implementations of the invention comprise also not explicitly cited combinations of features mentioned beforehand or hereinafter with regard to examples of the invention. Particularly, a skilled person will also add single aspects as improvements or supplements to the respective basic form of the present invention.

EXAMPLES

The present invention will now be described in detail with reference to several examples thereof. However, these examples are illustrative and do not limit the scope of the invention.

Example 1

General Procedure 1 to Prepare Racemic Nicotine 1.0 eq. of ethyl nicotinate, toluene (50.0 g or 4.4 parts by weight related to ethyl nicotinate) and optionally ethanol (1

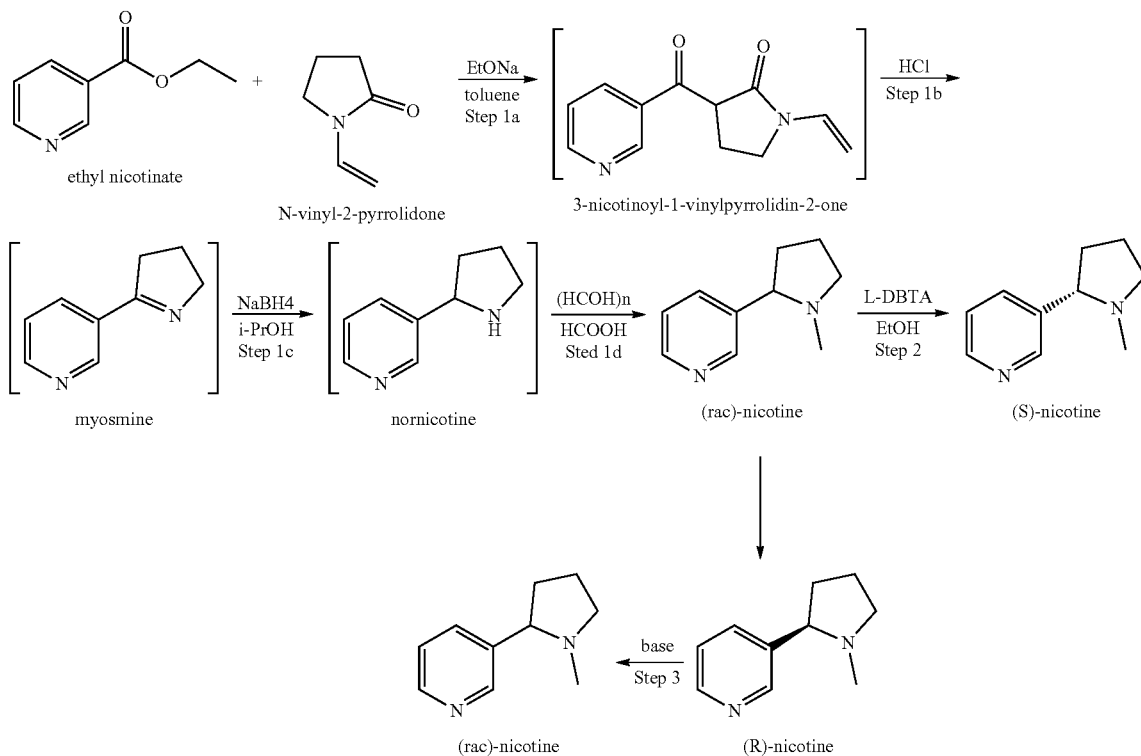

g, 0.09 parts by weight related to ethyl nicotinate), and 1.3 eq. of sodium ethoxide are heated under stirring to 80° C. to 85° C. 1.2 eq. of 1-vinyl-2-pyrrolidone (NVP) were charged to the reaction mixture at 80° C. to 85° C. during 1.5 to 2.0 hours under anhydrous conditions. The reaction was run at 95° C. to 100° for 3 hours. Then the reaction is completed, and the reaction mixture is distilled during 2 hours to remove some of the solvents (azeotrope containing 68 wt. % ethanol and 32 wt. % toluene). The remaining reaction mixture is poured on HCl (aq., 30% in water; 58.0 g or 4.4 eq.). Low-boiling components like acetaldehyde (from the "vinyl" component), ethanol and gaseous $CO_2$ were removed by distillation. When the reaction temperature reached 105° C., distillation was stopped and the reaction mixture was stirred at a temperature between 90° and 94° C. overnight. After completion of the reaction, the pH was adjusted to a value between 9.5 to 10.0 using NaOH (30% by weight in water). Iso-propanol (29.0 g, as given in Table 1a) and 1.0 eq. of $NaBH_4$ (in respect of the ethyl nicotinate) were charged in portions during 1 hour into the reaction vessel. The reaction was run at about 10° C. for more than 3 hours (at this point the content of myosmine was below 3.% by weight). Formic acid (HCOOH) was added, the reaction mixture was heated and formaldehyde ($H_2CHO$) was slowly added and the mixture was stirred at 60° C. After the reaction was finished (at this point the content of myosmine was below 0.5% by weight), the pH of the mixture was slowly adjusted to a value of 10.5 to 11.0 using NaOH (30% by weight in water) and stirring was carried out at 55° C. for 30 minutes until a phase separation is observed. The mixture was extracted twice with toluene. The combined organic phases were concentrated to obtain the crude product. By distillation of the crude product, racemic nicotine was obtained as a colorless oil, as shown in Table 1a.

General Procedure 2 to Prepare Racemic Nicotine 1.0 eq. of ethyl nicotinate, toluene, 1.6 eq. of sodium ethoxide, and 1.2 eq. of 1-vinyl-2-pyrrolidone (NVP) were charged into a flask at room temperature of about 20° C. under anhydrous conditions.

Then the reaction was run at 100° C. for 3 hours. The reaction was completed, and after the mixture had been cooled down to 30° C., HCl (36% by weight in water) was added dropwise. The low boiling components like acetaldehyde (from "vinyl"), ethanol and gaseous CO2 were removed by distillation, together with parts of the toluene and the water. When the reaction temperature reached 105° C., distillation was stopped and the reaction mixture was stirred at a temperature between 100° C. and 105° C. overnight. After completion of the reaction, the pH was adjusted to a value between 9.5 to 10.5 using NaOH (30% by weight in water). Iso-propanol and 1.0 eq. of $NaBH_4$ (in respect of the ethyl nicotinate) were charged into the reaction vessel. The reaction was run at room temperature (about 20° C.) for more than 3 hours (at this point the content of myosmine was below 3.0% by weight). Formic acid (HCOOH) and paraformaldehyde $((HCHO)_n)$ were added and the mixture was stirred at 65° C. for at least 3 hours. After the reaction was finished (at this point the content of myosmine was below 0.5% by weight), the pH of the mixture was adjusted to a value of 13 to 14 using NaOH (30% by weight in water). Water was added until all inorganic solids were dissolved. The mixture was extracted twice with toluene. The combined organic phases were concentrated to obtain the crude product. By distillation of the crude product, racemic nicotine was obtained as a colorless oil, as shown in Table 1b.

TABLE 1a

Results of a series of examples with varying amounts of formic acid and formaldehyde following general procedure 1.

| Ethyl Nicotinate g | HCl (aq 30%) g | i-prop. g | $NaBH_4$ g | HCOOH (aq 35%) g | ($H_2CO$) (aq 35%) g | Yield % | Purity % |
|---|---|---|---|---|---|---|---|
| 11.4 (1.0 eq) | 68.0 | 29.0 | 2.86 (1.0 eq) | 10.3 (3.0 eq) | 3.1 (1.0 eq) | 63.2 | 97.2 |
| 22.8 (1.0 eq) | 120.0 | 60.0 | 5.72 (1.0 eq) | 8.6 (2.5 eq) | 6.2 (1.0 eq) | 63.2 | 97.0 |
| 34.2 (1.0 eq) | 205.0 | 88.0 | 8.58 (1.0 eq) | 34.0 (3.3 eq) | 9.4 (1.0 eq) | 64.2 | 96.4 |
| 11.4 (1.0 eq) | 68.0 | 29.0 | 2.86 (1.0 eq) | 10.3 (3.0 eq) | 3.1 (1.0 eq) | 67.0 | 95.8 |

TABLE 1b

Results of a series of examples with varying amounts of formic acid and paraformaldehyde following general procedure 2.

| Ethyl Nicotinate g | HCl g | i-prop. g | $NaBH_4$ g | HCOOH g | $(HCHO)_n$ g | Yield % | Purity % |
|---|---|---|---|---|---|---|---|
| 11.4 (1.0 eq) | 36.0 | 20.0 | 2.86 (1.0 eq) | 10.3 (3.0 eq) | 4.5 (2.0 eq) | 46.0 | 99.7 |
| 11.4 (1.0 eq) | 36.0 | 20.0 | 2.86 (1.0 eq) | 10.3 (3.0 eq) | 4.5 (2.0 eq) | 46.0 | 98.9 |
| 68.4 (1.0 eq) | 216.0 | 48.0 | 17.2 (1.0 eq) | 61.8 (3.0 eq) | 13.5 (1.0 eq) | 51.8 | 99.8 |
| 68.4 (1.0 eq) | 216.0 | 48.0 | 17.2 (1.0 eq) | 61.8 (3.0 eq) | 13.5 (1.0 eq) | 49.6 | 98.7 |
| 68.4 (1.0 eq) | 216.0 | 48.0 | 17.2 (1.0 eq) | 31.0 (1.5 eq) | 16.2 (1.2 eq) | 45.5 | 99.2 |

TABLE 1b-continued

Results of a series of examples with varying amounts of formic acid and paraformaldehyde following general procedure 2.

| Ethyl Nicotinate g | HCl g | i-prop. g | NaBH$_4$ g | HCOOH g | (HCHO)$_n$ g | Yield % | Purity % |
|---|---|---|---|---|---|---|---|
| 205.2 (1.0 eq) | 648.0 | 360.0 | 51.6 (1.0 eq) | 124.0 (2.0 q) | 48.6 (1.2 eq) | 47.0 | 95.6 |
| 205.2 (1.0 eq) | 695.0 | 360.0 | 51.6 (1.0 eq) | 124.0 (2.0 eq) | 48.6 (1.2 eq) | 66.0 | 98.9 |
| 205.2 (1.0 eq) | 840.0 | 360.0 | 51.6 (1.0 eq) | 124.0 (2.0 eq) | 48.6 (1.2 eq) | 47.0 | 99.1 |
| 1436.4 (1.0 eq) | 4125.0 | 2500.0 | 432.0 (1.2 eq) | 1312.0 (3.0 eq) | 285.0 (1.0 eq) | 56.0 | 99.1 |
| 1437 (1.0 eq) | 4125.0 | 2500.0 | 432.0 (1.2 eq) | 875.0 (2.0 eq) | 313.0 (1.1 eq) | 59.7 | 97.5 |

In all cases exactly 1.2 eq NVP related to ethyl nicotinate, exactly 1.6 eq EtONa related to ethyl nicotinate, and 60.0 g toluene per 11.4 g ethyl nicotinate were used.

In the seventh sample of general procedure 2 with a yield of 66.0% denoted in Table 1b it should be noted that the mixture obtained by reacting ethyl nicotinate and NVP in toluene and sodium ethoxide was dropped to the aqueous HCl, and not as denoted above.

Example 2: Resolution Step 1.0 g racemic nicotine, as obtained by the previous examples, was mixed at room temperature with ethanol (1) and 2.2 g tartaric acid (DBTA) (1 equivalent). The mixture was refluxed for a few minutes and cooled down to room temperature (about 20° C.). Precipitation started, and the mixture was stirred overnight (10 to 12 hours) at 20° C. A precipitate that formed was filtered, washed with ethanol (2). The crude product was dissolved in ethanol (3). The mixture was refluxed for a few minutes and cooled down to room temperature. Precipitation started, and the mixture was stirred overnight (10 to 12 hours) at 20° C. The precipitate was filtered and washed with ethanol (4). The product was dried and the pure product was obtained.

3.2 g nicotine-L-DBTA as produced in Example 1b, sample 1, were suspended in 7.2 g water and 7.2 g toluene. Aqueous ammonia (25% by weight) was added until the pH was between 9.8 and 10.4. The phases were separated, and the aqueous phase was extracted twice with 2.4 g toluene. The toluene phases were combined, and toluene was removed by distillation. The residue was distilled under vacuum, yielding 0.93 g pure (S)-nicotine. Enantiopurity was determined by chiral HPLC.

Using different amounts as given in Table 2, similar resolution/separation experiments were carried out.

Molar equivalents of resolution agent and racemic nicotine have been used. The amount of ethanol is chosen as weight multiple of the racemic nicotine.

Furthermore, it was found that an increased yield and purity could be obtained with seeding at 40° C.

Example 3

Equivalent amounts of dibenzoyl-D-tartaric acid (23.2 g) and racemic nicotine (10.0 g) were dissolved in ethanol and stirred for 1 hour, refluxed for 15 minutes, cooled to room temperature and stirred for another hour. (R)-nicotine dibenzoyl-D-tartrate was obtained. After recrystallization in an iso-propanol-methanol mixture (1.0:0.3), (R)-nicotine was obtained. The results are given in the following Table 3.

TABLE 3 amounts for samples in Comparative Example 1

| DBTA | Ethanol | Yield | Chiral purity |
|---|---|---|---|
| 100% D-DBTA | 10.0 | 60.0% | 87.9% (S)-isomer |

Example 4: Racemisation Step

Nicotine recycled from the mother liquors, as obtained in Example 2 after separation of the (S)-nicotine, was rich in (R)-nicotine and typically showed a molar ratio of 70:30 (R:S), and thus was "racemised" as described below.

However, the racemization procedure described in the following paragraph is applicable for any mixture of (R)-nicotine and (S)-nicotine (R:S nicotine). The amount of nicotine may either be determined by analytical methods (e.g. quantitative HPLC) or estimated by the mass balance of

TABLE 2 samples of Example 2 using various amounts of solvents in steps 1, 2, 3 and 4

| | DBTA | Ethanol (1) | Ethanol (2) | Ethanol (3) | Ethanol (4) | Yield | Chiral purity |
|---|---|---|---|---|---|---|---|
| 1 | 100% L-DBTA | 10.0 | 2.5 | 5.0 | 2.5 | 67.6% | 99.8% (S)-isomer |
| 2 | 100% L-DBTA | 10.0 | 2.5 | 10.0 | 2.5 | 70.8% | 99.6% (S)-isomer |
| 3 | 90% L-DBTA 10% D-DBTA | 7.5 | 2.5 | 5.0 | 2.5 | 65.3% | 99.6% (S)-isomer | pure (S)-nicotine vs. nicotine input in the racemic resolution experiment, as described above.

All mother liquors from the resolution experiment are collected, and the solvent is removed by vacuum distillation. The residue is made alkaline (pH typically >12) by addition of aqueous NaOH (30% by weight).

The mixture is extracted with toluene—twice with 7 volumes with regard to the nicotine input. The toluene phases are combined, and the solvent is removed by distillation under ambient pressure.

Then 5% by weight of KO-tBu is added (with regard to the nicotine input) and the mixture is heated to 160° C. for 1 h. After this heat treatment nicotine is distilled off by vacuum distillation.

The recovered nicotine shows an enantiomeric excess >90%, i.e. has a molar ratio or (R)-nicotine to (S)-nicotine of from 55:45 to 45:55.

The mixture of the (R)- and (S)-nicotine can again be resolved using methods as disclosed in the corresponding examples.

The invention claimed is:

1. A method of preparing a compound of Formula I-a, comprising

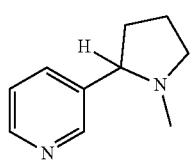

(I-a)

(i) reacting ethyl nicotinate and N-vinylpyrrolidone in the presence of an alcoholate base to 3-nicotinoyl-1-vinylpyrrolidin-2-one;
(ii) reacting the 3-nicotinoyl-1-vinylpyrrolidin-2-one with an acid to myosmine;
(iii) reducing the myosmine to nornicotine using a reducing agent; and
(iv) methylating the nornicotine to obtain the compound of formula I-a, wherein the method is carried out in a one-pot process.

2. The method of claim 1, wherein step (i) is carried out in the presence of an aromatic solvent.
3. The method of claim 2, wherein the aromatic solvent is benzene, toluene, or a mixture thereof.
4. The method of claim 1, wherein the alcoholate base in step (i) is an alkali metal alcoholate.
5. The method of claim 4, wherein the alkali metal alcoholate is chosen from sodium ethanolate, potassium ethanolate, and mixtures thereof.
6. The method of claim 1, wherein the alcoholate base is added in step (i) in an amount of between 1.4 and 2.0 equivalents, based on 1 equivalent of the ethyl nicotinate.
7. The method of claim 1, wherein step (ii) is carried out using an inorganic acid at a temperature between 90 and 115° C.
8. The method of claim 7, wherein the inorganic acid is HCl.
9. The method of claim 1, wherein step (iv) is carried out using formic acid and paraformaldehyde, or formic acid and formaldehyde.
10. The method of claim 1, wherein step (iii) is carried out using NaBH$_4$ as reducing agent.
11. The method of claim 1, further comprising reacting the compound of formula I-a with an organic base at a temperature between 140 and 160° C.
12. The method of claim 1, further comprising separating enantiomers of the compound of formula I-a by addition of a chiral O,O'-disubstituted tartaric acid.
13. The method of claim 12, wherein the dibenzoyl tartaric acid is a mixture of O,O'-dibenzoyl-L-tartaric acid (L-DBTA) and O,O'-dibenzoyl-D-tartaric acid (D-DBTA) with a molar ratio of L-DBTA to D-DBTA of 80:20 or more.
14. The method of claim 7, wherein step (ii) is carried out using an inorganic acid at a temperature between 100 and 105° C.
15. The method of claim 9, wherein step (iv) is carried out at a temperature between 40 and 95° C.
16. The method of claim 12, wherein the chiral O,O'-disubstituted tartaric acid is dibenzoyl tartaric acid.
17. The method of claim 16, wherein the dibenzoyl tartaric acid is O,O'-dibenzoyl-L-tartaric acid.

* * * * *